(12) United States Patent
Delenstarr

(10) Patent No.: US 6,832,163 B2
(45) Date of Patent: Dec. 14, 2004

(54) METHODS OF IDENTIFYING HETEROGENEOUS FEATURES IN AN IMAGE OF AN ARRAY

(75) Inventor: Glenda C. Delenstarr, Belmont, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 312 days.

(21) Appl. No.: 10/072,761

(22) Filed: Feb. 7, 2002

(65) Prior Publication Data

US 2004/0033622 A1 Feb. 19, 2004

Related U.S. Application Data

(60) Provisional application No. 60/268,115, filed on Feb. 9, 2001.

(51) Int. Cl.[7] ............................................... G06F 19/00
(52) U.S. Cl. ...................................................... 702/19
(58) Field of Search .......................................... 702/19

(56) References Cited

U.S. PATENT DOCUMENTS

| | | |
|---|---|---|
| 5,143,854 A | 9/1992 | Pirrung et al. |
| 5,631,734 A | 5/1997 | Stern et al. |
| 5,981,956 A | 11/1999 | Stern |

FOREIGN PATENT DOCUMENTS

| | | |
|---|---|---|
| WO | WO92/10092 | 6/1992 |

OTHER PUBLICATIONS

Wang et al. Quantitative quality control in microarray image processing and data acquisition. Nucleic Acids Research vol. 29, pp. e75, 1–8 (2001).*

Douglas Bassett et al "Gene expression informatics– it's all in your mine" Nature Genetics Supplement, vol. 21, Jan. 1999 pp. 51–55.

* cited by examiner

Primary Examiner—John S. Brusca

(57) ABSTRACT

Methods are provided for identifying heterogeneous features, including heterogeneous background regions, in an image of an array, e.g., in an image of a biopolymeric array, such as a nucleic acid array. The subject methods employ an algorithm that employs a different dispersity measure depending on whether the signal features are weaker or stronger. Also provided are computer readable storage media that include an algorithm capable of performing the steps of the subject methods. The subject methods find use in the processing of images obtained from a variety of different types of arrays, including nucleic acid arrays.

23 Claims, No Drawings

METHODS OF IDENTIFYING HETEROGENEOUS FEATURES IN AN IMAGE OF AN ARRAY

CROSS-REFERENCE TO RELATED APPLICATIONS

This application claims priority under 35 U.S.C. § 119(e) to U.S. Provisional Application Ser. No. 60/268,115 filed on Feb. 9, 2001; the disclosure of which is herein incorporated by reference.

INTRODUCTION

1. Field of the Invention

The field of this invention is biopolymeric arrays, and particularly image analysis of biopolymeric arrays.

2. Background of the Invention

Biopolymeric arrays, e.g., nucleic acid arrays, are increasingly important tools in the life science research and related fields, both in industry and academia. While significant advances in array design have been made over the last decade, processing of array images continues to be a challenge.

A variety of software tools and protocols have been developed for use in processing array images. The basic goal of such protocols is to reduce an image of spots of varying intensities into a table with a measure of the intensity (or the ratio of intensities for multi-colored fluorescence images) for each spot. While these goals are straightforward, there is no common method for obtaining these goals. Furthermore, scanning and image processing protocols currently available are resource intensive, and often require human intervention to properly grid the images and flag features that should be excluded from subsequent analysis, e.g., features that exceed a heterogeneity threshold.

With respect to flagging of features for analysis exclusion, one reason to exclude such features is feature heterogeneity. The problem of feature heterogeneity affects all analytical methods that are based upon detecting and reporting the signal of a region of interest, such as signals from a feature from a nucleic acid array, e.g., an oligonucleotide or cDNA array. Bright pixels in an otherwise low signal feature lead to overestimation of the signal. Dark pixels (e.g., from scratches) in an otherwise high signal feature lead to underestimation of the signal. Features that have a high degree of heterogeneity also yield signals that have a low degree of confidence, where the intra-feature or feature inter-pixel standard deviation of the signal is very high.

Many currently employed image analysis protocols use local background regions for background subtraction of the features on the array. The use of a local background region that is contaminated with high signal pixels leads to overestimating the background and underestimating the net signal of features. These problems can occur where either a 1:1 local background:feature or a global statistical value is employed.

An approach currently employed to identify heterogeneous features is manual curation of the image. In manual curation of an image, a user views the scanned image of an array and either notes individual feature numbers or positions or uses customized software tools to mark the features as "bad" so that down-stream data analysis will see the features as flagged and adjust its use accordingly. Manual curation suffers from the fact that it is highly subjective and unwieldy for arrays of high feature counts.

As such, there is continued interest and need for the development of new methods for identifying features in an image of an array as heterogeneous. Of particular interest would be the development of such a method which could be performed automatically without human intervention to consistently identify heterogeneous features in an array image, where the method was suitable for processing images obtained for nucleic acid and other biopolymeric arrays.

Relevant Literature

Bassett et al., Nature Genetics Supp. (January 1999) 21: 51–55, provides a review of the problems of array image processing. Patents of interest include: U.S. Pat. Nos. 5,143,854; 5,631,734 and 5,981,956. See also WO 92/10092.

SUMMARY OF THE INVENTION

Methods are provided for identifying heterogeneous features, including heterogeneous background features, in an image of an array, e.g., in an image of a biopolymeric array, such as a nucleic acid array. The subject methods employ an algorithm that employs a different dispersity measure depending on whether the signal features are weaker or stronger. In the subject methods, a toggle parameter, e.g., a single value (i.e., toggle point) or range of values (i.e., toggle range, smooth function), for the array of features is first determined. The toggle parameter is determined using statistics obtained from low signal features on the array. Following determination of the toggle parameter, those features that have a signal intensity that is either: (a) equal to or less than the toggle parameter and have an intra-feature noise metric 1 level, e.g., standard deviation, that exceeds the intra-feature noise limit for metric 1; or (b) greater than the toggle point and have an intra-feature noise metric 2 level that exceeds the intra-feature noise limit for metric 2, e.g., coefficient of variation; are identified as heterogeneous. Also provided are computer readable storage media that include an algorithm capable of performing the steps of the subject methods. The subject methods find use in the processing of images obtained from a variety of different types of arrays, including nucleic acid arrays.

DESCRIPTION OF THE SPECIFIC EMBODIMENTS

Methods are provided for identifying heterogeneous features, including heterogeneous background features, in an image of an array, e.g., in an image of a biopolymeric array, such as a nucleic acid array. The subject methods employ an algorithm that employs a different dispersity measure depending on whether the signal features are weaker or stronger. In the subject methods, a toggle parameter, e.g., a single value (i.e., toggle point) or range of values (i.e., toggle range, smooth function), for the array of features is first determined. The toggle parameter is determined using statistics obtained from low signal features on the array. Following determination of the toggle parameter, those features that have a signal intensity that is either: (a) equal to or less than the toggle parameter and have an intra-feature noise metric 1 level, e.g., standard deviation, that exceeds the intra-feature noise limit for metric 1; or (b) greater than the toggle point and have an intra-feature noise metric 2 level that exceeds the intra-feature noise limit for metric 2, e.g., coefficient of variation; are identified as heterogeneous. The subject methods may also be used to identify heterogenous local background regions. Also provided are computer readable storage media that include an algorithm capable of performing the steps of the subject methods. The subject methods find use in the processing of images obtained from a variety of different types of arrays, including nucleic acid arrays.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

As summarized above, the subject invention provides methods for identifying heterogeneous features and background regions in an array of features. Specifically, the subject invention provides methods of identifying heterogeneous features and background regions in an image of an array of features, where the image is typically a scanned image of an array of biopolymeric agents. The array of biopolymeric agents is typically an array of probe biopolymeric agents to which has been bound labeled biopolymeric targets. The biopolymeric agents may, in principle, be a variety of different compounds, but are generally polypeptides, e.g., proteins, or nucleic acids, e.g., oligonucleotides or cDNAs, where in many embodiments the arrays are arrays of nucleic acids. The target that is bound to the probe on the array, e.g., the hybridized nucleic acid target on a nucleic acid array, is typically labeled with a detectable label, where the label may be directly or indirectly detectable, and the target may be labeled before or after hybridization, so long as it provides an image indicative of a bound target on the array when the image of the array is obtained. Labels that find use in the field of arrays include isotopic labels, fluorescent labels, and the like.

The image of the array that is evaluated or processed with the subject methods is typically an image that is scanned into an electronic storage medium of a computing means. Devices and protocols for scanning an array to produce an electronic image of the array vary depending on a number of parameters, including the nature of the array, the nature of the target label, and the like, where methods and devices for performing this step are well known in the art. See for example U.S. Pat. Nos. 5,143,854; 5,631,734 and 5,981,956; the disclosures of which are herein incorporated by reference. See also WO 92/10092.

Array images that may be processed to identify heterogeneous features according to the subject methods may vary greatly with respect to the number of individual features in the image. As such, the subject methods are suitable for processing images of both low feature and high feature number. In many embodiments, the number of features that are present on images that are processed by the subject methods range is at least about 10, usually at least about 50 and more usually at least about 100, where the number of features may be as high as 500; 1,000; 10,000; 25,000; or higher. Array images that may be processed according to the subject methods may include both features and background regions, where the features may be low, intermediate and high signal features (F). The low features include a subset of features, the background features (BF), that consistently have low signal and that are used in the outlier algorithm of this invention. An array for use with the present invention will generally be constructed such that the ratio of hybridization features to background features is between about 1 to about 10,000, often between about 10 to about 5,000, and in many embodiments between about 50 to about 2,000. In many embodiments, there will be one background feature for every 50 to every 2,000 hybridization featureson the array.

In the subject methods, a different dispersity measure, based on an iterative algorithm, is employed to determine whether a given feature or background region should or should not be flagged as heterogenous. The dispersity measure depends on whether the signal of the features or background regions are weak or strong. The toggle parameter is the method used in this invention to determine whether the signal is weak or strong and thus which dispersity measure is to be used. The first step in the subject methods is to determine (i.e., derive, generate, etc.) a toggle parameter for the image being processed. As mentioned above, the toggle parameter may be a single value, i.e., a toggle point, or a range of values (e.g., a smooth function) that includes at least two values or points. The toggle parameter is used, in conjunction with an intra-feature noise metric_1, e.g., standard deviation, or an intra-feature noise metric_2, e.g., coefficient of variation (i.e. the standard deviation divided by the mean), to determine whether a feature is to be evaluated as a heterogeneous feature. The toggle parameter indicates whether the variance of a feature derives primarily from: (a) a combination of a constant variance component (e.g., instrument), which is independent of signal, and a Poisson component (e.g. statistics of counting photons), which is dependent upon the signal; or from (b) a variable variance which is primarily dominated by synthesis, labeling, and hybridization noise.

In those embodiments where the toggle parameter is a toggle point, the intra-feature noise metric_1 can be the intra-feature standard deviation (i.e. inter-pixel standard deviation, or SD) and the intra-feature noise metric_2 can be the intra-feature coefficient of variation (i.e. the intra-feature SD divided by the feature mean). The toggle point is determined in the subject methods from low signal features and background regions in the array. By low signal features in the array image is meant those features of the array that have a signal that is in the same signal range as the signal range of the set of background features (BF), or within a defined multiplier of the that signal range. For a detailed description of the use of background features in array based assays, see U.S. patent Ser. No. 09/398,399, the disclosure of which is herein incorporated by reference. Typically, the maximum signal of this range is less than 10%, usually less than 5%, and more usually less than 1% of the maximum signal of all the features in the array. The set of low signal features typically has a noise metric, e.g., (standard deviation or SD), which is less than 100-times, usually less than 50-times, and more usually less than 20-times the minimum noise metric, e.g., SD, of the instrument.

The low signal features that are used to determine the toggle parameter are, in many embodiments, identified as follows. Each feature (i.e., feature corresponding to a target/probe complex on the array surface, "F") and local background region (i.e., "LB") on the array image is composed of a number of pixels in the scanned image. The number of pixels comprising each feature and comprising the local background region is sufficient to provide for an adequate and meaningful number of data points for each feature and local background region. The size of each given pixel is substantially less than the size of the feature to which it corresponds, where the size of each pixel is typically less than about 20$\mu$, and is usually at least about 5$\mu$, often at least about 10$\mu$, and the number of pixels per features typically is at least about 50 and may be as great as about 100 or more. The feature mean and feature standard deviation for each feature (i.e., F_Mean and F_SD, respectively) and local background region (i.e., LB_Mean and LB_SD, respectively) of the entire image is then determined. In other words, for each feature and background region of the array image, the signal of each pixel in the feature or region is detected and both the mean and standard deviation are then determined from the collection of pixels comprising that feature or background region.

Following determination of the mean and standard deviation for each feature and local background region on the array, the minimum mean (i.e., Min_Mean) and minimum standard deviation (i.e., Min_SD) for the array is determined. In certain embodiments, features with saturated pixels are excluded in these particular determination steps. See e.g., Algorithm II provided in the Experimental Section, infra. In certain embodiments, the minimum mean is either the lowest F_Mean value of the array image or the lowest LB_Mean value for the array. Alternatively, the lowest defined percentile, such as 0.5 percentile, of signal could be used. In yet other embodiments, the mean or median from the instrument dark scan is used as the minimum mean for the image.

Next, the minimum standard deviation (i.e., Min_SD) of the array image is determined. The minimum standard deviation is either the lowest F_SD value or the lowest LB_SD value of the image. Finally, the minimum variance (i.e., Min_Var) for the array image is determined by squaring the previously determined minimum standard deviation. Following the above steps yields a minimum mean, standard deviation and variance for the array, i.e., Min_Mean, Min_SD and Min_Var. This process is repeated for data from each channel (e.g. red and green channels).

A net mean (i.e., F_Net_Mean), variation (i.e., F_Net_Var), standard deviation (i.e., F_Net_SD) and coefficient of variance (F_Net_CV) is then determined for each feature and background region on the array using the above obtained minimum mean, standard deviation and variance values. Specifically, a net feature mean for each feature on the array is determined by subtracting the above determined minimum mean from the feature mean. Likewise, a net variance is determined for each feature on the array by squaring the standard deviation of each feature and then subtracting the minimum variance from the squared value. A net standard deviation is then determined for each feature by taking the square root of the net variance for each feature. Finally, a net coefficient of variance is determined for each feature by dividing the net standard deviation for each feature by that feature's net mean. The same method is used to calculate the net mean, net standard deviation, and net coefficient of variance for each background region of the array. Prior to the next step, a linear regression toggle (i.e., Lin_Reg_Toggle) value is determined. The linear regression toggle value is determined by multiplying the minimum standard deviation (i.e., Min_SD) by a multiplier, where the multiplier typically ranges form about 1 to 30, usually from about 2 to 10 and in many embodiments is 3, to first obtain an initial standard deviation limit (i.e., Initial_SD_Limit). This initial standard deviation limit is then divided by a linear regression coefficient of variation limit (i.e., Lin_Reg_CV_Limit) to obtain the linear regression toggle. The linear regression coefficient of variation limit typically ranges from about 0.05 to 0.90, usually from about 0.20 to 0.80 and more usually from about 0.40 to 0.70.

Where multiple background feature sequences are used, each having replicate features, a t-test may be included in this step to determine whether the signal from all sequences are representative of the same distribution. That is, if there is more than one sequence used for background features, only the sequence sets are used which are not different from the set with the lowest mean. See the alternative Algorithm II provided in the Experimental Section, infra. Alternatively, the Mann-Whitney ranking test can be used, instead of the t-test.

Alternatively, the Initial_SD_Limit can be calculated based upon the population statistics of the background features. For example, using the background features from the sequences passing the above t-test, one can determine the Xth-percentile of the net standard deviations of that population of background features. The percentile, X, typically ranges between 0 and 100, usually from 5 to 90, and more usually from 50 to 75. The example shown in Algorithm III uses the $75^{th}$ percentile (i.e., BF_SD_Percentile). The Initial_SD_Limit is then set to the maximum of this (Xth-percentile of net standard deviations value) and the (3*Min_SD value), determined in the Algorithm I example, above.

The next step in the subject methods is to identify those background features that are to be used in the linear regression calculation of the toggle point. In this step, all background features (i.e., BF) that fit within the following parameters are retained for use in subsequent calculations (as described in greater detail below): (a) those features whose net signal mean (F_Net_Mean) is less than or equal to, i.e., does not exceed, the linear regression toggle value and whose net standard deviation (F_Net_SD) is less than the initial standard deviation limit; and (b) those features whose net mean (F_Net_Mean) is greater than the linear regression toggle value and whose net coefficient of variation (F_Net_CV) is less than the linear regression coefficient of variation limit. As such, a set of background features is identified whose net mean signal is either: (a) less than or equal to, i.e., does not exceed, the linear regression toggle value and whose net standard deviation is less than the initial standard deviation limit; or (b) those features whose net mean is greater than the linear regression toggle value and whose net coefficient of variation is less than the linear regression coefficient of variation limit. Background features meeting the above criteria are considered to be within the inlier set of the initial population of background features. All background features that do not meet the above criteria (i.e., the outlier set) are not used in the following calculations, i.e., they are removed from further consideration.

The resultant inlier set of background values (i.e., BF_Inlier_Set) is used to determine a maximum net mean value (i.e., Max_Net_Mean). Specifically, the highest net mean signal of any member feature of the background feature inlier set identified above (i.e., the net mean from the background feature in the set which is the largest) is multiplied by a factor (i.e., Max_Mult) to obtain the maximum net mean value. The factor with which the background feature net mean is multiplied to arrive at the maximum net mean value, i.e., the Max_Mult, generally ranges from about 1 to 10, usually from about 1 to 4 and more usually from about 2 to 3, where in many embodiments the factor is 2. Alternatively, the Max_Net_Mean may be determined using the inter-quartile range of Net_Means of the BF_Inlier_Set, as employed in Algorithm II, infra.

The above obtained maximum net mean values are then employed to obtain the set of low signal features in the array image from which the toggle point is derived. Specifically, all of the features on the array are screened to identify those features that have a net mean (i.e., F_Net_Mean) that does not exceed, i.e., is less than or equal to, the maximum net mean. In other words, a set of low signal features is identified in which the net mean of member features of the set does not exceed the maximum net mean value identified above.

Of this identified set of low signal features (i.e., Low_Mean_Features), the next step is to identify those members of this set that are subsequently used in the linear regression analysis from which the toggle point is generated. Features of this set identified for use in the linear regression analysis described below are those features: (a) whose net mean does not exceed, i.e., is less than or equal to, the linear regression toggle and whose net standard deviation is less than the initial standard deviation limit; and (b) whose net mean is greater than or exceeds the linear regression toggle and whose coefficient of variation is less than the linear regression coefficient of variation limit. In other words, an inlier set of low signal features (i.e., Low_F_Inlier_Set) is identified from the initial set of low signal features, where each member of the inlier set is a feature: (a) whose net mean is less than or equal to, i.e., does not exceed, the linear regression toggle value and whose net standard deviation is less than the initial standard deviation limit; or (b) whose net mean is greater than the linear regression toggle value and whose net coefficient of variation is less than the linear regression coefficient of variation limit.

The above identified inlier sets of low signal features, i.e., the union of the inlier background feature set and the low signal feature set or {BF_Inlier_Set & Low_F_Inlier_Set} is then used in the following linear regression calculations from which the toggle point (i.e., Toggle_Point) is derived. First, the standard deviation (F_SD) and net mean (F_Net_Mean) for each feature in the above described inlier set of features and background features is then plotted, with standard deviation or SD being the Y value and net mean being the X value. The method of least squares is then employed to identify the straight line that best fits the X and Y values of the plotted set, i.e., to identify the linear regression of the plotted set. It is important to note that the linear regression can be done as a calculation without doing the plot. In other words, the plot is useful to visualize the data, but is not required The slope of the resultant linear regression (i.e., Low_Mean_Slope) and the Y intercept (i.e., Low_Mean_Y_Int) are then used in the following toggle point derivation calculations.

First, the maximum residual (i.e., SD_Max_Dev) of the observed intra-feature standard deviation from the linear regression calculated intra-feature standard deviation (i.e., SD_Calc) for the above set of inlier features is determined. For each feature in the set, the expected intra-feature standard deviation from the above linear regression is first calculated; where the expected intra-feature standard deviation is equal to the low mean Y intercept plus the product of the low mean slope and the net mean of the feature. Residuals are calculated by subtracting the observed intra-feature standard deviation from the expected intra-feature standard deviation for each member of the union set of BF_Inliers and Low_F_Inliers. The maximum residual is then determined from this set of residuals.

Alternatively, a confidence interval of the linear regression, rather than SD_Max_Dev, may be used to calculate the line that determines the toggle intersect point. In this alternative embodiment, this inlier set of low signal features is employed to calculate the linear regression standard error of the estimate (SEE) for the intra-feature SD vs. signal. The SEE is multiplied by a constant (SEE_Mult) to estimate a prediction interval for the linear regression fit. See Algorithm II in the Experimental Section, infra.

The resultant maximum residual (or the prediction interval if SEE is employed) is then used in conjunction with the above derived low signal linear regression values (i.e., low mean slope, low mean Y intercept) to derive or determine the toggle point as follows. First, a toggle line (Toggle_Line) is calculated. The slope of the toggle line is the low mean slope and the Y intercept of the toggle line is the sum of the low mean Y intercept and the maximum residual value (or the prediction interval if SEE is employed), as described above. Next, a high signal line (i.e., High_Signal_Line) is calculated. The high signal line has a slope which is equal to the high signal coefficient of variation limit (i.e., High_Signal_CV_Limit) and a Y intercept generally set to 0. The high signal coefficient of variation limit may vary, but generally ranges from about 0.05 to 0.70, usually from about 0.10 to 0.50 and more usually from about 0.20 to 0.40, and in many embodiments is 0.40. The intersection between the toggle line and the high signal line is then identified and employed as the toggle point (i.e., Toggle_Point) in the following steps. As such, the toggle point is equal to (toggle Y intercept-high signal Y intercept)/(high signal slope-toggle slope) or (Toggle_Y_Int-High_S_Y_Int)/(High_S_Slope-Toggle_Slope).

Alternatively, the Toggle_Point can be bounded by an upper and lower limit. An example is to use a Toggle_Point_Bound calculation, e.g., the product of a multiplier (TogglePt_Mult) and the Max_Net_Mean. If the Toggle_Point, calculated in the above section and described in Algorithm I, is less than 0 or if it exceeds the Toggle_Point_Bound value, then the Toggle_Point_Bound value is used for the Toggle_Point. The TogglePt_Mult may vary, but generally ranges from about 0 to 10, usually from about 1 to 5 and more usually from about 2 to 4, and in many embodiments is 3.5. See Algorithm III in the Experimental Section, infra.

The above identified toggle point is then employed in the final step of the subject process to identify those features of the array image that are heterogeneous. All of the array probe features are then evaluated to identify those features that: (a) have a net mean signal that does not exceed the toggle point, i.e., is less than or equal to the toggle point, and have a net standard deviation that exceeds the standard deviation limit; and (b) have a net mean signal that exceeds the toggle point and have a net coefficient of variation that exceeds the high signal coefficient of variation limit. In other words, the image features are screened to identify those features that either: (a) have a net mean that does not exceed the toggle point, i.e., is less than or equal to the toggle point, and have a net standard deviation that exceeds the standard deviation limit; and (b) have a net mean that exceeds the toggle point and have a net coefficient of variation that exceeds the high signal coefficient of variation limit. These features are then labeled as heterogeneous. The same method is applied to the local background regions to determine which ones are labeled as heterogenous.

In the above step of using the toggle point to identify those features that are heterogeneous, the standard deviation limit (SD_Limit) that is employed may vary. Thus, in some embodiments the standard deviation limit is a constant value which is equal to the sum of: (a) the product of toggle slope and the toggle point, and (b) the toggle Y intercept. In yet other embodiments, the standard deviation limit may be a value calculated from a limit line, e.g. where the line equals the sum of: (a) the product of the toggle slope and the net signal; and (b) the toggle Y intercept. In yet other embodiments, the standard deviation limit may be a value calculated from a limit hyperbola, where the hyperbola is equal to the square root of the sum of the product of the (net mean multiplied by the high signal CV limit) squared and the toggle Y intercept squared.

The above image processing method readily identifies those features in an array that are heterogeneous. Generally, the above described method is carried out automatically by a computing means pursuant to the directions of an algorithm which specifies and directs the above process steps. In such embodiments, one need only enter into the computing means the following information: (a) probe feature mean, probe feature standard deviation, local background mean and local background standard deviation, where these values may be obtained from a image feature extraction algorithm which automatically processes an image to obtain these values; (b) a list of features in the image that are background features; (c) and the following variable limits: (i) linear regression coefficient of variation limit; (ii) maximum multiplier; and (iii) high signal coefficient of variation limit. Where an algorithm such as Algorithm II is employed, the following additional variable limits are entered: (iv) Max_Sat_Pix, which may range from about 0 to 50, usually from about 0 to 5, but in many embodiments is 0 (v); IQR_Mult, which may range from about 1 to 10, usually from about 2 to 3, but in many embodiments is 3; (vi) SEE_Mult, which may range from about 1 to 10, usually from about 2 to 5, but in many embodiments is 3; and (vii) Bkgd_SD_Mult, which may range from about 1 to 10, usually from about 1 to 3, but in many embodiments is 1. Representative specific algorithms for identifying heterogeneous features in an array image using the above information or input data are provided in the Experimental Section infra.

Alternative embodiments of the above described method are also provided by the present invention. In certain alternative embodiments, the median is used to estimate the signal value of a feature, instead of the mean. In yet other embodiments, the median of absolute deviations is used instead of the standard deviation to estimate the inter-pixel noise of a feature. In yet other embodiments, the inter-quartile range is used instead of the standard deviation to estimate the inter-pixel noise of a feature. In yet other embodiments, the difference between the median and the mean is used instead of the standard deviation to estimate the inter-pixel noise of a feature. In yet other embodiments, the median of absolute deviations divided by the median is used instead of the coefficient of variation to estimate the inter-pixel noise of a feature. In yet other embodiments, the inter-quartile range divided by the median is used instead of the coefficient of variation to estimate the inter-pixel noise of a feature. In yet other embodiments, the difference between the median and the mean is divided by the median and is used instead of the coefficient of variation to estimate the inter-pixel noise of a feature. In yet other embodiments, robust regression methods are used instead of linear least squares regression (e.g. for the calculation of the Low_Mean_Slope and Low_Mean_Y_Int). In yet other embodiments, robust error methods associated with robust regression methods are used, instead of using the standard error of the estimate (e.g., for the calculation of the Toggle_Y_Int). The above set of alternative embodiments are "robust" statistical methods.

In yet other embodiments, the scanning instrument's dark scan is employed as the minimum for the probe and background features. In yet other embodiments, the population of local background regions is used instead of the population of background features to determine the Max_Net_Mean, which is used to determine the toggle point. In yet other embodiments, a continuous function, utilizing the Toggle_Y_Int, the Toggle_Slope, and the High_S_Slope, and including the variable square-root of the signal, or other piece-wise fits, spline-fits, and other continuous functions are employed as being the limit line separating heterogeneous outliers from inliers.

Also provided by the subject invention is a computer readable storage medium on which is recorded an algorithm for carrying out the above described process, such as the one appearing in the Experimental Section infra. The computer readable storage medium may be any convenient medium, including CD, DAT, floppy disk, etc.

Where a given specific array is to be read with a given specific scanner, a given predetermined toggle parameter, e.g., toggle point, for the specific array/scanner pair may be employed, such that the above derivation of the toggle parameter need not be employed. As such, also provided are methods of processing an array image to identify heterogeneous features using a predetermined toggle parameter.

The subject methods find use applications in which an image of an array is employed. Specifically, the subject methods find use in identifying those features of an array image that are heterogenous and may be excluded in image evaluation. As such, the subject methods find use in a variety applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Where the arrays are arrays of polypeptide binding agents, e.g., protein arrays, specific applications of interest include analyte detection/proteomics applications, including those described in: U.S. Pat. Nos. 4,591,570; 5,171,695; 5,436,170; 5,486,452; 5,532,128; and 6,197,599; the disclosures of which are herein incorporated by reference; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

As such, in performing an array-based assay using the methods of the subject invention, the array will typically be exposed to a sample (for example, a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER scanner available from Agilent Technologies, Palo Alto, Calif. Other suitable apparatus and methods are described in U.S. patent applications Ser. No. 09/846125 "Reading Multi-Featured Arrays" by Dorsel et al.; and U.S. Pat. No. 6,406,849 "Interrogating Multi-Featured Arrays" by Dorsel et al. As previously mentioned, these references are incorporated herein by reference. The observed array images are processed according to the present methods. In addition, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

The following examples are offered by way of illustration and not by way of limitation.

---

EXPERIMENTAL

A.  Algorithm I
    Algorithm Details:
1) CALCULATE        [offsets to be subtracted from signals and intra-feature SD's]
Using all features and local background regions:
Min_Mean        = minimum (F_Mean, LB_Mean)
                    [In the future the mean or median from the instrument
                    dark scan may be used instead]
Using all features and local background regions:
Min_SD          = minimun (F_SD, LB_SD), using all features and local background
                  regions
Min_Var         = Min_SD*Min_SD
Using all features:
F_Net_Mean      = (F_Mean–Min_Mean)
F_Net_Var       = (F_SD)*(F_SD)–Min_Var
F_Net_SD        = Square root (F_Net_Var)
F_Net_CV        = (F_Net_SD/F_Net_Mean)
Initial_SD_Limit        =3*Min_SD
Lin_Reg_Toggle = Initial_SD_Limit/Lin_Reg_CV_Limit
2) Filter
[For each background feature, determine whether or not it will be used in the linear
regression calculation.]
BF_Inlier_Set =
{
{IF (F_Net_Mean<=Lin_Reg_Toggle) & IF (F_Net_SD<Initial_SD-Limit)}
OR
[IF (F-Net_Mean>Lin_Reg_Toggle) & IF (F_Net_CV<Lin_Reg_CV_Limit)}
}
***Note: the above equations were used to clarify the use of a toggle point; that is, to
distinguish between teh absolute SD and CV limit regions. The same algorithm
could be simplified to:
{IF (F_Net_SD<Initial_SD_Limit) OR IF (F_Net_CV<Lin_Reg_CV_Limit)}

-continued

EXPERIMENTAL

3) CALCULATE [Maximum signal of features to be used in linear regression calculation.]
Using BF_Inlier_Set:
Max_Net_Mean = maximum (F_Net_Mean) * Max_Mult
[The Max_Mult constant allows a greater number of features that represent Region B to be included in the linear regression calculations.]
4) FILTER
Using all features:
Low_Mean_Features = set of features with {F_Net_Mean<=Max_Net_Mean}
5) FILTER
[For each low mean feature, determine whether or not it will be used in the linear regression calculation.]
Using Low_Mean_Features:
Calculation Low_F_Inlier_Set=
{
{IF (F_Net_Mean <= Lin_Reg_Toggle) & IF (F_Net_SD <Initial_SD_Limit}
OR
{IF (F_Net_Mean > Lin_Reg_Toggle) & IF (Low_F_Net_CV < Lin_Reg_CV_Limit)}
}
6) CALCULATE [Linear Regression calculations.]
Using union set of {BF_Inlier_Set & Low_F_Inlier_Set}
Low_Mean_Slope     = linear regression slope of (Y = F_SD, X = F_Net_Mean)
Low_Mean_Y_Int     = linear regression y-intercept of (Y = F_SD, X = F_Net_Mean)
7) CALCULATE [Upper boundary line calculations.]
SD_Calc            = expected intra-feature SD from above linear regression:
                   = (Low_Mean_Slope * F_Net_Mean) + Low_Mean_Y_Int
SD_Max_Dev         = maximum of deviations (i.e. residual) between
                     observed and expected intra-feature SD:
                     Maximum (F_SD-SD_Calc)
Toggle Line        Toggle_Slope = Low_Mean_Slope
                   Toggle_Y_Int = (Low_Mean_Y_Int + SD_Max_Dev_)
High_Signal_Line   High_S_Slope = High_Signal_CV_Limit
                   High_S_Y_Int = 0
Toggle_Point       = intersection between Toggle_Line and High_Signal_Line:
                   (Toggle_Y_Int − High_S_Y_Int)/(High_S_Slope − Toggle_Slope)
SD-Limit
[can use a constant, a value calculated from a limit line, or a value calculated from a limit hyperbola]
          1) Constant    =(Toggle_Slope*Toggle_Point) + Toggle_Y_Int
          or,
          2) Line        =(Toggle_Slope * Net_Signal) + Toggle_Int
          or,
          3) Hyperbola   =square-root {(F_Net_Mean*
          High_Signal_CV_Limit)$^2$ + (Toggle_Y_Int)$^2$}
8) DETERMINE INTRA-FEATURE_OUTLIERS:
For each feature on array:
IF (F_Net_Mean<=Toggle_Point)
    IF (F_Net_SD, SD_Limit)
        THEN, Feature = INTRA_FEATURE_INLIER
        ELSE, Feature = INTRA_FEATURE_OUTLIER
ELSE,
IF(F_Net_Mean>Toggle_Point)
    IF(F_Net_CV<High_Signal_CV_Limit)
        THEN, Feature=INTRA_FEATURE_INLIER
        ELSE, Feature=INTRA_FEATURE_OUTLIER
***Note: the above equations were used to clarify the use of a toggle point; that is, to distinguish between the absolute SD and CV limit regions. The same algorithm could be simplified to:
{
IF(F_Net_SD<SD_Limit) OR IF (F_Net_CV < High_Signal_CV_Limit)
        THEN, Feature=INTRA_FEATURE_INLIER
        ELSE, Feature=INTRA_FEATURE_OULIER
}
B.   Algorithm II
1) CALCULATE         [Offsets to be subtracted from signals and intra-feature SD's]
Find set of feature whose pixels satisfy the maximum limit percentage of saturated pixels:
gFeature_Set        = all feature whose (gNumPix//NumPix) <= Max_Sat_Pix
rFeature_Set        = all feature whose (rNumPix/NumPix) <= Max_Sat_Pix
Perform for each color channel using the appropriate Feature_Set:
Using the features from the appropriate color channel Feature_Set:
Min_Mean            = minimum (F_Mean, LB_Mean)
Min_SD              = minimum (F_SD, LB_SD)
Min_Var             = Min_SD*Min_SD
Using all features:
F_Net_Mean          = (F_Mean − Min_Mean)
F_Net_Var           = (F_SD)*(F_SD) − Min_Var -continued

EXPERIMENTAL

F_Net_SD         = Square root (F_Net_Var)
F_Net_CV         = (F_Net_SD/F_Net_Mean)
Initial_SD_Limit = 3*Min_SD
Lin_Reg_Toggle   = Initial_SD_Limit/Lin_Reg_CV_Limit
2) FILTER
(a) [For each background feature sequence, determine whether or not it wil be used
in the BF_Inlier_Set determination (step 2b).]
If there are two different sequence being used for background features, use a t-test
to determined if the signals of the features from BF_sequence_1 are from the same
distribution as the signals of the feature from BF_sequence_2:
    IF the signals of the features from BF_sequence_1 are from the same
    distribution as the signals of the features from BF_sequence_2,
        THEN use the feature from both BF_sequences in the BF_Inlier_Set
        determination;
    ELSE,
        The feature from the BF_sequence with the lower mean will be used
    in the BF_Inlier_Set determination; and the features from the BF_sequence
    with the higher mean will be used in the Low_Mean_Features determination
    (step 4).
(b) [For each background feature, determine whether or not it will be used in the
linear regression calculation.]
BF_Inlier_Set =
{
{IF (F_Net_Mean <= Lin_Reg_Toggle) & IF (F_Net_SD < Initial_SD_Limit)}
OR
{IF (F_Net_Mean > Lin_Reg_Toggle) & IF (F_Net_CV < Lin_Reg_CV_Limit)}
}
***Note: the above equations were used to clarify the use of a toggle point; that is, to
distinguish between the absolute SD and CV limit regions. The same algorithm
could be simplified to:
{IF (F_Net_SD < Initial_SD_Limit) OR IF (F_Net_CV < Lin_Reg_CV_Limit)}
3) CALCULATE     [Maximum signal of features to be used in linear regression
calculation.]Using BF_Inlier_Set:
Upper_BF         = (75%'tile) = IQR * IQR_Mult
Max_Net_Mean     = Upper_BF * Max_Mult
[The Max_Mult constant allows a greater number of features that represent Region
B to be included in the linear regression calculations.]
4) FILTER
Using all features:
Low_Mean_Features = set of features with {F_Net_Mean <= Max_Net_Mean}
5) FILTER
[For each low mean feature, determine whether or not it will be used in the linear
regression calculation.]
Using Low_Mean_Features:
Calculate Low_F_Inlier_Set =
{
{IF (F_Net_Mean <= Lin_Reg_Toggle) & IF (F_Net_SD < Initial_SD_Limit)}
OR
{IF (F_Net_Mean > Lin_Reg_Toggle) & IF (Low_F_Net_CV < Lin_Reg_CV_Limit)}
}
6) CALCULATE     [Linear Regression calculations.]
Using union set of {BF_Inlier_Set & Low_F_Inlier_Set}:
Low_Mean_Slope   = linear regression slope of (Y = F_SD, X= F_Net_Mean)
Low_Mean_Y_Int   = linear regression y-intercept of (Y = F_SD, X= F_Net_Mean)
7) CALCULATE     [Upper boundary line calculations.]
SD_Calc          = expected intra-feature SD from above linear regression:
                Using union set of {BF_Inlier_Set & Low_F_Inlier_Set}:
                = (Low_Mean_Slope * F_Net_Mean) + Low_Mean_Y_Int
SEE (Standard Error of the Estimate):    Square root of the {Sum of squared
residuals between calculated and observed SD's}:
                Using union set of {BF_Inlier_Set & Low_F_Inlier_Set}:
                = Sqrt {SUM (SD_Calc − F_Net_SD)}
Toggle_Line      Toggle Slope    = Low_Mean_Slope
                Toggle_Y_Int= (Low_Mean_Y_Int + (SEE* SEE_Mult) )
High_Signal_Line High_S_Slope    = High_Signal_CV_Limit
                High_S_Y_Int    = 0 (default)
Toggle_Point     = intersection between Toggle_Line and High_Signal_Line:
                (Toggle_Y_Int − High_S_Y_Int)/(High_S_Slope −
Toggle_Slope)
SD_Limit         {to be used for features)
                1) Constant    = (Toggle_Slope *Toggle_Point) = Toggle_Y_Int
                or,
                2) Line        = (Toggle_Slope *Net_Signal) + Toggle_Y_Int
                or,
                3) Hyperbola   = square-root {(F_Net_Mean*
                High_Signal_CV_Limit)$^2$ + (Toggle_Y_Int)$^2$}

| -continued |
|---|
| EXPERIMENTAL |

```
Bkgd_SD_Limit      {to be used for backgrounds)
                   = Bkgd_SD_Mult * SD_Limit
8) DETERMINE INTRA-FEATURE NON-UNIFORMITY_OUTLIERS:
For each feature on array:
IF (F_Net_Mean <= Toggle_Point)
    IF (F_Net_SD < SD_Limit)
        THEN,      Feature = INTRA_FEATURE NON-
    UNIFORMITY_INLIER
        ELSE,      Feature = INTRA_FEATURE NON-
    UNIFORMITY_OUTLIER
ELSE,
IF (F_Net_Mean > Toggle_Point)
    IF (F_Net_CV < High_Signal_CV_Limit)
        THEN,      Feature = INTRA_FEATURE NON-
    UNIFORMITY_INLIER
        ELSE,      Feature = INTRA_FEATURE NON-
    UNIFORMITY_OUTLIER
For each background region on array:
IF (F_Net_Mean <= Toggle_Point)
    IF (F_Net_SD < Bkgd_SD_Limit)
        THEN,      Background = NON-UNIFORMITY_INLIER
        ELSE,      Background = NON-UNIFORMITY_OUTLIER
ELSE,
IF (F_Net_Mean > Toggle_Point)
    IF (F_Net_CV < High_Signal_CV_Limit)
        THEN,      Background = NON-UNIFORMITY_INLIER
        ELSE,      Background = NON-UNIFORMITY_OUTLIER
***Note: the above equations were used to clarify the use of a toggle point; that is, to
distinguish between the absolute SD and CV limit regions. The same algorithm
could be simplified to:
{
IF (F_Net_SD < SD_Limit) OR IF (F_Net_CV < High_Signal_CV_Limit)
        THEN,      Feature = INTRA_FEATURE_INLIER
        ELSE,      Feature = INTRA_FEATURE_OUTLIER
}
C.    Algorithm III.
Input:
    From feature extraction: intra-feature/region (inter-pixels) statistics for every
    feature and local background region on array:
        Feature mean (F_Mean)
        Feature standard deviation (F_SD)
        Local Background mean (LB_Mean)
        Local Background standard deviation (LB_SD)
    From array design:
        List of feature corresponding to background feature (BF)
    Variable limits:
        Max_Sat_Pix (default = 0)
        BF_SD_Percentile (default = 75%)
        Lin_Reg_CV_Limit (default = 0.40)
        Max_Mult (default = 2)
        IQR_Mult (default = 3)
        SEE_Mult (default = 3)
        High_Signal_CV_Limit (default = 0.25)
        High_S_Y_Int (default = 0)
        TogglePt_Mult (default = 3.5)
        Bkgd_SD_Mult (default = 1)
Algorithm Details:
1) CALCULATE    [Offsets to be subtracted from signals and intra-feature SD's]
Find set of feature whose pixels satisfy the maximum limit percentage of saturated
pixels:
gFeature_Set     = all features whose (gNumPix//NumPix) <= Max_Sat_Pix
rFeature_Set     = all features whose (rNumPix/NumPix) <=Max_Sat_Pix
Perform for each color channel using the appropriate Feature_Set:
Using the features from the appropriate color channel Feature_Set:
Min_Mean         = minimum (F_Mean, LB_Mean)
Min_SD           = minimum (F_SD, LB_SD)
Min_Var          = Min_SD*Min_SD
Using all features:
F_Net_Mean       = (F_Mean − Min_Mean)
F_Net_Var        = (F_SD)*(F_SD) − Min_Var
F_Net_SD         = Square root (F_Net_Var)
F_Net_CV         = (F_Net_SD/F_Net_Mean)
2) FILTER
(a) [For each background feature sequence, determine whether or not it will be used
in the BF_Inlier_Set determination (step 2b).]
```

-continued

EXPERIMENTAL

If there are two different sequences being used for background features, use a t-test
to determine if the signals of the features from BF_sequence_1 are from the same
distribution as the signals of the features from BF_sequence_2:
    IF the signals of the features from BF_sequence_1 are from the same
    distribution as the signals of the feature from BF_sequence_2,
    THEN use the features from both BF_sequences in the BF_Inlier_Set
    determination;
    ELSE,
        The features from the BF_sequence with the lower mean will be used
    in the BF_Inlier_Set determination; and the features from the BF_sequence
    with the higher mean will be used in the Low_Mean_Features determination
    (step 4).
(b) Calculate variables:
BF_SD_Limit        = BF_SD_Percentile of the F_Net_SD's using the
                    BF_Sequences that pass the above-test
Initial_SD_Limit     = MAX { (3*Min_SD) or (BF_SD_Limit)}
Lin_Reg_Toggle      = Initial_SD_Limit/Lin_Reg_CV_Limit
(c) [For each background feature, determine whether or not it will be used in the
linear regression calculation.]
BF_Inlier_Set =
{
{IF (F_Net_Mean <= Lin_Reg_Toggle) & IF (F_Net_SD < Initial_SD_Limit)}
OR
{IF (F_Net_Mean > Lin_Reg_Toggle) & IF (F_Net_CV < Lin_Reg_CV_Limit)}
}
***Note: the above equations were used to clarify the use of a toggle point; that is, to
distinguish between the absolute SD and CV limit regions. The same algorithm
could be simplified to:
{IF (F_Net_SD < Initial_SD_Limit) OR IF (F_Net_CV < Lin_Reg_CV_Limit)}
3) CALCULATE      [Maximum signal of features to be used in linear regression
calculation.]Using BF_Inlier_Set:
Upper_BF             = (75%'tile) + IQR * IQR_Mult
Max_Net_Mean       = Upper_BF * Max_Mult
[The Max_Mult constant allows a greater number of features that represent Region
B to be included in the linear regression calculations.]
4) FILTER
Using all features:
Low_Mean_Features      = set of features with {F_Net_Mean <= Max_Net_Mean}
5) FILTER
[For each low mean feature, determine whether or not it will be used in the linear
regression calculations.]
Using Low_Mean_Features:
Calculate Low_F_Inlier_Set =
{
{IF (F_Net_Mean <= Lin_Reg_Toggle) & IF (F_Net_SD < Initial_SD_Limit)}
OR
{IF (F_Net_Mean > Lin_Reg_Toggle) & IF (Low_F_Net_CV < Lin_Reg_CV_Limit)}
}
6) CACULATE       [Linear Regression calculations.]
Using union set of {BF_Inlier_Set & Low_F_Inlier_Set}:
Low_Mean_Slope    = linear regression slope of (Y= F_SD, X= F_Net_Mean)
Low_Mean_Y_Int    = linear regression y-intercept of (Y= F_SD, X= F_Net_Mean)
7) CALCULATE      [Upper boundary line calculations.]
SD_Calc              = expected intra-feature SD from above linear regression:
                    Using union set of {BF_Inlier_Set & Low_F_Inlier_Set}:
                    = (Low_Mean_Slope * F_Net_Mean) + Low_Mean_Y_Int
SEE(Standard Error of the Estimate):    Square root of the {Sum of squared
residuals between calculated and observed SD's}:
                    Using union set of {BF_Inlier_Set & Low_F_Inlier_Set}:
                    = Sqrt {SUM (SD_Calc − F_Net_SD)}
Toggle_Line          Toggle_Slope  = Low_Mean_Slope
                    Toggle_Y_Int= (Low_Mean_Y_Int + (SEE* SEE_Mult) )
High_Signal_Line     High_S_Slope =High_Signal_CV_Limit
Toggle_Point_Calc    = intersection between Toggle_Line and High_Signal_Line:
                    (Toggle_Y_Int − High_S_Y_Int)/(High_S_Slope −
                    Toggle_Slope)
Toggle_Point_Bound    = TogglePt_Mult * Max_Net_Mean
Toggle_Point         = If Toggle_Point_Calc > 0, then MIN {Toggle_Point_Calc or
                    Toggle_Point_Bound}
                    ELSE, = Toggle_Point_Bound
SD_Limit             {to be used for features)
use a constant, a value calculated from a limit line, or a value calculated from
        a limit hyperbola
                4) Constant     = (Toggle_Slope*Toggle_Point) + Toggle_Y_Int
                or,
                5) Line         = (Toggle_Slope*Net_Signal) + Toggle_Y_Int
                or, -continued

EXPERIMENTAL

```
                6) Hyperbola    = square-root {(F_Net_Mean*
                                 High_Signal_CV_Limit)² + (Toggle_Y_Int)² }
Bkgd_SD_Limit   {to be used for backgrounds)
                = Bkgd_SD_Mult * SD_Limit
8) DETERMINE INTRA-FEATURE NON-UNIFORMITY_OUTLIERS:
For each feature on array:
IF (F_Net_Mean <= Toggle_Point)
    IF (F_Net_SD < SD_Limit)
        THEN,       Feature = INTRA_FEATURE NON-
    UNIFORMITY_INLIER
        ELSE,       Feature = INTRA_FEATURE NON-
    UNIFORMITY_OUTLIER
ELSE,
IF (F_Net_Mean > Toggle_Point)
    IF (F_Net_CV < High_Signal_CV_Limit)
        THEN,       Feature = INTRA_FEATURE NON-
    UNIFORMITY_INLIER
        ELSE,       Feature = INTRA_FEATURE NON-
    UNIFORMITY_OUTLIER
For each background region on array:
IF (F_Net_Mean <= Toggle_Point)
    IF (F_Net_SD < Bkgd_SD_Limit)
        THEN,       Background = NON-UNIFORMITY_INLIER
        ELSE,       Background = NON-UNIFORMITY_OUTLIER
ELSE,
IF (F_Net_Mean > Toggle_Point)
    IF (F_Net_CV < High_Signal_CV_Limit)
        THEN,       Background = NON-UNIFORMITY_INLIER
        ELSE,       Background = NON-UNIFORMITY_OUTLIER
***Note: the above equations were used to clarify the use of a toggle point; that is, to
distinguish between the absolute SD and CV limit regions. The same algorithm
could be simplified to:
{
IF (F_Net_SD < SD_Limit) OR IF (F_Net_CV < High_Signal_CV_Limit)
        THEN,       Feature = INTRA_FEATURE_INLIER
        ELSE,       Feature = INTRA_FEATURE_OUTLIER
}
```

It is evident from the above results and discussion that an important new method for processing images of arrays is provided by the subject invention. Specifically, the subject invention provides an automatic method for identifying heterogeneous features and local background regions in an array image accurately, quickly and reproducibly. As such, the subject invention represents a significant contribution to the art.

All publications and patent application cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of identifying heterogeneous features in an image of an array of features, said method comprising:
    (a) determining a toggle parameter for said array of features; and
    (b) identifying features as heterogeneous that:
        (i) have a signal intensity that is equal to or less than the toggle parameter and has a first intra-feature noise metric that exceeds a first intra-feature noise metric limit; or
        (ii) have a signal intensity that is greater than the toggle parameter and has a second intra-feature noise metric that exceeds the second intra-feature noise metric limit;
    whereby heterogeneous features in said image are identified.

2. The method according to claim 1, wherein said first intra-feature noise metric is intra-feature standard deviation and said second intra-feature noise metric is intra-feature coefficient of variation.

3. The method according to claim 1, wherein said image is an image of a biopolymeric array.

4. The method according to claim 1, wherein said toggle parameter is a toggle point.

5. The method according to claim 4, wherein said toggle point is determined from statistics obtained from low signal features of said array.

6. The method according to claim 5, wherein said toggle point is the intersection of a toggle line and a high signal coefficient of variation limit.

7. A method of identifying heterogeneous features in an image of a nucleic acid array, said method comprising:
    (a) determining a toggle point for said image; and
    (b) identifying features as heterogeneous that:
        (i) have a signal intensity that is less than or equal to said toggle point and have an intra-feature standard deviation that exceeds a standard deviation limit; or
        (ii) have a signal intensity that exceeds said toggle point and have an intra-feature coefficient of variation that exceeds a coefficient of variation limit;
    whereby heterogeneous features in said image of said nucleic acid array are identified.

8. The method according to claim 7, wherein said toggle point is determined from statistics obtained from low signal features.

9. The method according to claim 7, wherein said toggle point determination comprises deriving a toggle line from said low signal feature statistics.

10. The method according to claim 9, wherein said toggle point is the intersection of said toggle line and a high signal coefficient of variation limit.

11. A method of identifying heterogeneous features in an image of a nucleic acid array, said method comprising:
 (a) determining a toggle point for said array of features from statistics obtained from low signal features of said image; and
 (b) identifying features as heterogeneous that:
  (i) have a signal intensity that is less than or equal to said toggle point and have an intra-feature standard deviation that exceeds a standard deviation limit; or
  (ii) have a signal intensity that exceeds said toggle point and have an intra-feature coefficient of variation that exceeds a coefficient of variation limit;
 whereby heterogeneous features in said image of said nucleic acid array are identified.

12. The method according to claim 11, wherein said toggle point determination comprises deriving a toggle line from said low signal feature statistics.

13. The method according to claim 12, wherein said toggle point is the intersection of said toggle line and a high signal coefficient of variation limit.

14. A computer readable storage medium on which is recorded an algorithm for identifying heterogeneous image features in an image of an array, wherein said algorithm performs the steps of:
 (a) determining a toggle point for said image; and
 (b) identifying features as heterogeneous that:
  (i) have a signal intensity that is less than or equal to said toggle point and have an intra-feature standard deviation that exceeds a standard deviation limit; or
  (ii) have a signal intensity that exceeds said toggle point and have an intra-feature coefficient of variation that exceeds a coefficient of variation limit.

15. The computer readable storage medium according to claim 14, wherein said image is an image of a biopolymeric array.

16. The computer readable storage medium according to claim 15, wherein said biopolymeric array is a nucleic acid array.

17. The computer readable storage medium according to claim 14, wherein said toggle point is determined from statistics obtained from low signal features.

18. The computer readable storage medium according to claim 17, wherein said toggle point determination comprises deriving a toggle line from said low signal feature statistics.

19. The computer readable storage medium according to claim 18, wherein said toggle point is the intersection of said toggle line and a high signal coefficient of variation limit.

20. A method of detecting the presence of an analyte in a sample, said method comprising:
 (a) contacting (i) a biopolymeric array having a polymeric ligand that specifically binds to said analyte, with (ii) a sample suspected of comprising said analyte under conditions sufficient for binding of said analyte to a biopolymeric ligand on said array to occur;
 (b) detecting the presence of binding complexes on the surface of the said array to obtain assay data in the form of an array image;
 (c) processing said array image to identify heterogenous features according to the method of claim 1;
 (d) employing said processed array image to detect the presence of said analyte in said sample.

21. The method according to claim 20, wherein said method further comprises a data transmission step in which a result from a reading of the array is transmitted from a first location to a second location.

22. A method according to claim 21 wherein said second location is a remote location.

23. A method comprising receiving data representing a result of a reading obtained by the method of claim 20.

* * * * *